United States Patent
Fuller et al.

(10) Patent No.: US 10,481,067 B2
(45) Date of Patent: Nov. 19, 2019

(54) DETECTING AND LOCATING FLUID FLOW IN SUBTERRANEAN ROCK FORMATIONS

(75) Inventors: Brian Fuller, Littleton, CO (US); John Marcus Sterling, Houston, TX (US); Les G. Engelbrecht, Littleton, CO (US)

(73) Assignee: Sigma Cubed Inc., Houston, TX (US)

( * ) Notice: Subject to any disclaimer, the term of this patent is extended or adjusted under 35 U.S.C. 154(b) by 1169 days.

(21) Appl. No.: 13/382,871

(22) PCT Filed: Jul. 7, 2010

(86) PCT No.: PCT/US2010/041252
§ 371 (c)(1),
(2), (4) Date: Jan. 6, 2012

(87) PCT Pub. No.: WO2011/005888
PCT Pub. Date: Jan. 13, 2011

(65) Prior Publication Data
US 2012/0116681 A1    May 10, 2012

Related U.S. Application Data

(60) Provisional application No. 61/223,666, filed on Jul. 7, 2009, provisional application No. 61/353,527, filed on Jun. 10, 2010.

(51) Int. Cl.
| | | |
|---|---|---|
| G01N 15/08 | (2006.01) | |
| G01V 1/28 | (2006.01) | |
| G01V 1/42 | (2006.01) | |
| E21B 47/022 | (2012.01) | |

(52) U.S. Cl.
CPC .................................. *G01N 15/08* (2013.01)

(58) Field of Classification Search
CPC ................................ G01N 15/08; G01V 1/42
USPC ........................................................ 702/12–18
See application file for complete search history.

(56) References Cited

U.S. PATENT DOCUMENTS

| 5,987,244 A * | 11/1999 | Kau et al. ..................... 713/500 |
| 2008/0033656 A1 * | 2/2008 | Herwanger ..................... 702/18 |
| 2009/0067286 A1 * | 3/2009 | Bose et al. ..................... 367/38 |

* cited by examiner

*Primary Examiner* — Alexander Satanovsky
(74) *Attorney, Agent, or Firm* — Greenberg Traurig LLP; Dwayne Mason; Lennie Bersh

(57) ABSTRACT

A method and system includes acquiring a seismic dataset while fluids are injected into the subsurface with seismic data recorded at multiple sensor locations. Seismic travel times are computed between sensors and subsurface locations using a velocity model. Travel times and travel time delays between pairs of sensors may be used as input to determine a similarity coefficient associated with subsurface positions. The similarity coefficients are determined using cross correlation, semblance calculations or eigenstructure decomposition. The coefficient values are related to the acoustic response at each subsurface position and may be summed together for each position for comparison with other subsurface positions to determine the position of a fluid front moving through the subsurface. The values may be displayed to illustrate the position of fluids in the subsurface and displayed to show the time variance of the fluid position.

14 Claims, 9 Drawing Sheets

DETECTING AND LOCATING FLUID FLOW IN SUBTERRANEAN ROCK FORMATIONS

CROSS-REFERENCE TO RELATED APPLICATION

This application claims the benefit of U.S. Provisional Application No. 61/223,666 filed 7 Jul. 2010 and U.S. Provisional Application No. 61/353,527 filed 30 Jun. 2010 both of which are incorporated herein for all purposes.

BACKGROUND

Technical Field

The present disclosure generally relates to methods and systems for investigating subterranean formations, and particularly to locating fluid flow in subterranean formations.

Background Information

Hydraulic fracture stimulation is an economically important technology applied to oil and gas reservoirs to increase oil and gas production. Fracturing technology has dramatically increased the available hydrocarbon reserves of the United States over the past several years, particularly its natural gas reserves. During hydraulic fracture stimulation highly pressurized fluids are injected into reservoir rock. The pressurized fluids overcome the breaking strength of the rock and generate fractures that act as pathways by which oil and natural gas can migrate to the borehole and be brought to the surface. The injected fluids, which may reach volumes of 4,000 gallons per minute or more, flow through fractures created by the high-pressure fluids and through previously existing natural fractures in the rock.

SUMMARY

The following presents a general summary of some of the many possible embodiments of this disclosure in order to provide a basic understanding of this disclosure. This summary is not an extensive overview of all embodiments of this disclosure. This summary is not intended to identify key or critical elements of the disclosure or to delineate or otherwise limit the scope of the claims. The following summary merely presents some concepts of the disclosure in a general form as a prelude to the more detailed description that follows.

In one non-limiting embodiment of seismic data processing disclosed herein, the method includes acquiring a seismic dataset while injecting fluids into rock in the subsurface, for example in fracture stimulation of a hydrocarbon reservoir. Seismic waves are generated by this fluid injection. Seismic data are recorded before, during and after the fluid injections at multiple spatial locations. Spatial locations may be on the surface or often more advantageously below the surface in a well bore. Seismic travel times are computed between points of interest, for example the seismic receivers and any subsurface point on a grid of points developed with velocity model of the subsurface. Grids, which may be 2-D grids or 3-D volumetric grids, may be regularly spaced or irregularly spaced, any geometric configuration, for example cubic or quadratic grids, tetrahedral grids, grids in spherical, cylindrical or Cartesian coordinates. Travel times or travel time differences between pairs of receivers may be used as input to determine a cross correlation coefficient for individual node positions of a subsurface velocity grid/model. Alternatively a plurality of receiver positions may be used as input to a semblance or eigenstructure decomposition multichannel algorithm. The travel time comparisons between sensors at different positions or levels are used to determine 'zero-lag' time data recording positions or initial time positions for determining data time series sequences that are input for crosscorrelations, eigenstructure decomposition or other signal subspace methods. In this manner the sensors may be 'aimed' or 'steered' towards each position in the subsurface grid such that a total acoustic energy response may be determined for each node or earth subsurface position and the signal energy extraction enhanced by using longer periods of time series sequences. The coefficient values may be used to determine a value associated with acoustic energy at each node or subsurface position. These coefficient values may be summed together or otherwise compared with other subsurface node positions to determine the position a fluid front moving through the subsurface. For each point of interest, such as grid nodes, computed values of the crosscorrelations may be summed that are delayed from the zero lag by a time equal to the time difference between the associated receiver locations and the point of interest. The results may be displayed to determine the position of fluids in the subsurface. Alternatively the eigenstructure decomposition or semblance values or coefficients associated with the subsurface fluid positions are determined.

BRIEF DESCRIPTION OF THE DRAWINGS

The following drawings illustrate some of many possible embodiments in order to provide a basic understanding of this disclosure. These drawings do not provide an extensive overview of all embodiments of this disclosure. These drawings are not intended to identify key or critical elements of the disclosure or to delineate or otherwise limit the scope of the claims. The following drawings merely present some concepts of the disclosure in a general form. Thus, for a detailed understanding of this disclosure, reference should be made to the following detailed description, taken in conjunction with the accompanying drawings, in which like elements have been given like numerals.

DETAILED DESCRIPTION

Figure 1:
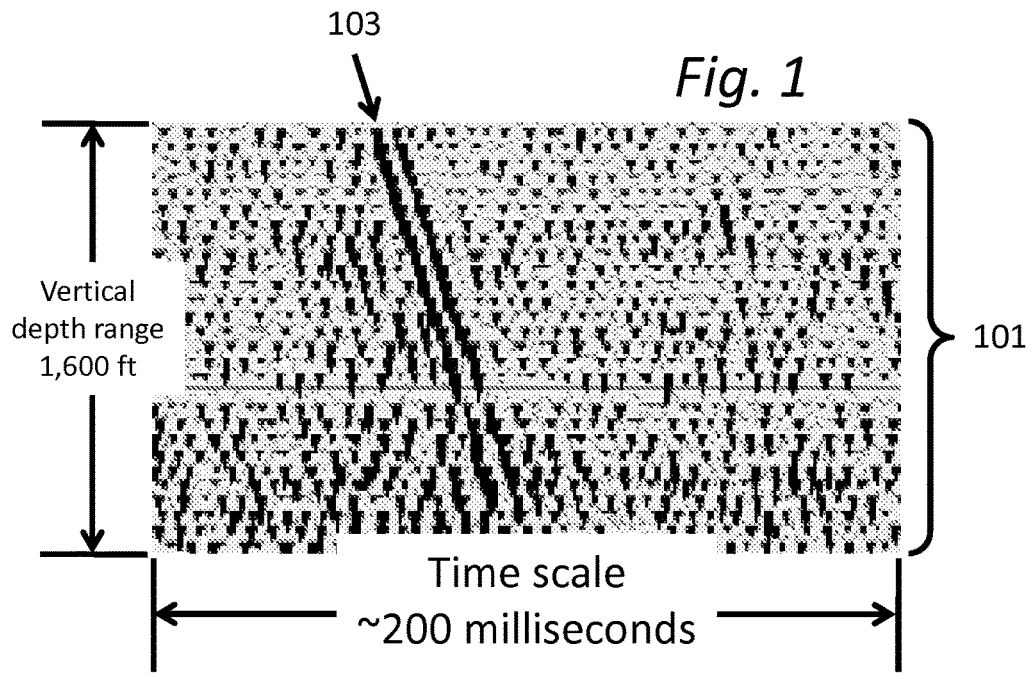
FIG. 1 illustrates a 200 ms seismic data recording of an impulsive seismic event (that could be the result of tensile failure) recorded on seismic borehole receivers distributed over a vertical space of approximately 1,600 ft.

Non-limiting illustrative embodiments of methods or systems for determining subsurface reservoir parameters are presented through one or more various aspects such as those disclosed below. Particular non-limiting embodiments related to fluid flow detection and determining fluid flow position in subterranean formations are described.

Embodiments disclosed herein and equivalents that will be apparent to practitioners in the art provide for robustly estimating position and changes in seismic properties associated with movement of fluids through subsurface reservoirs. Oil, gas, and water flow through reservoirs as these fluids are produced from or injected into the subsurface. Subsequent changes in fluid saturation and pressure likewise produce changes in seismic properties. Collocated timelapse seismic surveys are recorded to image these changes in saturation and pressure, indicated indirectly through changes in seismic properties. Methods and systems as described herein improve imaging of the location and magnitude of these changes, leading to improved understanding of flow through the reservoir and optimized recovery of hydrocarbons.

Embodiments described herein are seismic data processing methods designed to directly detect and determine the locations at which fluids flow in a rock formation. Detection is enabled due to locating acoustic energy produced by the movement of fluids through the subsurface. Knowledge of where injected fluids flow in the reservoir during stimulation is of significant value to petroleum engineers in that it can allow them to know specifically which parts of the reservoir were contacted by fracture stimulation operations. Remedial actions can then be taken, such as drilling additional wells and running more fracture stimulation treatments to drain parts of the reservoir that were not fractured by the initial fracture stimulation operation. The remedial actions can significantly increase the efficiency of oil and gas recovery from the reservoir and decrease the necessity of developing new or more expensive sources of energy.

Subsurface investigation and mapping technology related to the embodiments disclosed herein are methods of microseismic or seismic fracture mapping. In microseismic methods as practiced in contrast to embodiments described herein, small earthquakes, or "microseisms", which occur in response to injection of fluid in the reservoir are analyzed directly. These discrete seismic events (see example in FIG. 1) are recorded by seismometers placed in the nearby area. Through a variety of data processing methods the location, or focus, of the small earthquakes can determined. The locations at which the rocks break in response to high-pressure fluid injection are inferred to be locations at which fracture stimulation fluids have flowed into the reservoir rock. In contrast, the inputs to embodiments disclosed herein are not dependent on whether discrete seismic events are visible on seismic records.

The inference of fluid flow locations from microseisms or seismic fracture mapping is indirect and incomplete. For example it has been observed that in some cases rocks do not generate observable seismic events during fluid injection even though large volumes of fluid are injected into the reservoir and hydrocarbons subsequently produced from the reservoir. Thus it is clear that fluid pathways were created in the reservoir as a result of hydraulic fracture stimulation but the discrete seismic events related to breaking rocks, events that many microseismic mapping methods are dependent upon, were not observed.

During hydraulic reservoir stimulation the injected fluids are forced through a constricted space (fractures in rocks). Resonant and otherwise dynamic and vibratory behavior of the fluids in the rocks occurs as pressure waves imparted to surrounding rock as fluids interact with the rock media and the random tortuous fluid pathways in the reservoir rock. The resonant action could even include a random or chaotic component due to damping of the oscillating system as the surrounding rock absorbs the acoustic energy. Regardless of the exact resonant and vibratory characteristics, seismic waves are generated by fluid flow through the formation and propagated through the rock over a time period that extends up to many hours during fluid injection as well as after pumping is concluded. The seismic signal can be recorded on appropriately placed seismometers and inverted as outlined in embodiments disclosed herein to determine the location of fluid flow, as well as the position of the fluid flow front, in the reservoir regardless of whether seismic events are observable in the seismic recordings.

The seismic signal generated by fluid flowing through a restricted space, here called a fluid flow seismic signal, may appear to have a different nature than is observed when rocks break in response to fracture stimulation. In many cases the fluid flow seismic signal may not be apparent or observable by visually examining seismic records. The fluid flow seismic signal is a low-amplitude continuous, semi-continuous or intermittent signal recorded over relatively long periods of time rather than the relatively brief higher-amplitude signal of a few milliseconds duration recorded when rocks break. Methods for detecting and locating seismic events resulting from tensile failure are inadequate for determining the fluid flow seismic signal, and therefore the fluid flow location within the rocks, even the though the fluid flow may initiate the tensile failure resulting in rock breaks. It has been observed that fluid injection to a formation can cause tensile failure at locations distant from the actual fluid pathway. So while tensile failure may represent a change in the subsurface stress regime, these microseisms may be only marginally useful for determining actual fluid flow location in the subsurface. Embodiments herein are directed to seismic signal processing methods that directly detect fluid flow positions through the subsurface based upon relatively low-amplitude seismic signals that are continuously radiated from locations at which fluid flows through a restricted space.

In contrast to embodiments presented herein, event-picking microseismic location methods rely upon discrete, short time duration signal represented in the seismic section illustrated in FIG. 1. These are often referred to as "triggers." Embodiments presented here are based upon seismic signals generated and recorded over longer periods of time and that are often of low amplitude relative to the discrete microseism events. The low-amplitude seismic signals used by embodiments herein may not, in general, be recognized in unprocessed seismic data and will in general be considered as ambient background energy or unusable noise that cannot be used in the microseismic methods dependent on discrete or identifiable events within seismic recordings.

FIG. 1 illustrates a recording 101 using many sensors at several levels in a borehole of an impulsive seismic event 103 (that could be the result of tensile failure) recorded on seismic receivers distributed over a vertical space of approximately 1,600 feet. Each seismic trace (horizontal time series) represents the acoustic energy recorded at one depth level. The seismic event traverses the seismic receivers from near the center bottom of the figure toward the upper left of FIG. 1. This is an example of the type of seismic signals used in commonly-practiced microseismic event location methods. The seismic waves shown in this event 103 occur over a few milliseconds of time and generally stand out against the background environmental signal and noise that is observed elsewhere in seismic records.

Detection of the fluid flow within a reservoir as disclosed herein is not reliant upon the type of high-amplitude discrete seismic signal 103 illustrated in FIG. 1, although various embodiments of the method use these data that includes these signals as they may contribute energy to overall fluid flow seismic signal location. Instead, this invention uses lower-amplitude seismic signals generated by fluid motion over much longer periods of time to detect the locations at which fluid flows or other changes in reservoir rock occur that generate seismic signals over a relatively long time period (many seconds to many minutes). The time periods selected for data processing may include using seismic traces of 10 to 20 minutes in length. Selecting seismic data with respect to phase is not required for processing embodiments disclosed herein.

The fluid flow location information derived from the methods disclosed here is of great value to petroleum engineers who can optimize production from reservoirs based on determining where fracture stimulation fluids have accurately been observed within the subsurface.

One or more signal decomposition or signal enhancement, extraction or analysis methods may be used in embodiments presented herein. The methods include multichannel methods such as crosscorrelation, semblance and eigenstructure decomposition. Crosscorrelation used illustratively herein will be understood as an example of multichannel signal subspace methods, which may also be used in various embodiments. Crosscorrelation, which may be performed in the time or frequency domain, is generally known to practitioners of the geophysical or signal processing arts. Equation 1 below expresses a commonly used form of time-domain crosscorrelation.

$$C(z)=a(t)*d(t)=\Sigma a(t)*d(t-z)$$ Equation 1

In Equation 1 the variables $a(t)$ and $d(t)$ represent digital time series. The output of the crosscorrelation, $C(z)$, is a third digital time series that is the crosscorrelation between $d(t)$ and $a(t)$ and is a time-variant measure of similarity between the signal in $a(t)$ and the signal that is within the time-variant function $d(t)$. $C(z)$ may be referred to as similarity coefficients.

The relative time delays between receiver locations and points in the subsurface are generally computed via a travel time computation algorithm such as a ray-trace or wave-field-propagation program. Such computational methods are well-known to those who practice the art of seismic imaging. Seismic travel times between two points, say points A and B, are obtained using knowledge of the velocity field between the points, for example a seismic velocity model. The model should reflect as closely as possible the seismic velocities of the earth in the nearby region of the points A and B. Such velocity fields can include anisotropic terms and three-dimensional velocity variations.

An example use of crosscorrelation is the oil and gas exploration method known as Vibroseis. In the Vibroseis technique heavy trucks with special hydraulic equipment are used as a seismic source to propagate a known seismic signal into the earth over a time period varying from a few seconds to many tens of seconds. Seismometers in proximity to the seismic source are used to record seismic signals reflected from rock layers deep in the earth. Vibroseis seismic reflection signals recorded by seismometers are not generally useful in the form of the original recording because the seismic signal that they record is spread over a long period of time and useful signal is not easily recognizable or observable in the seismic data in that form. Application of the crosscorrelation method to the seismic data however is used to extract the signal known to have been input to the earth from the recorded seismic signal. The crosscorrelation method essentially extracts and compresses the long-period input signal into a seismic signal of short time duration but high seismic energy. The result is a seismic signal that might have been observed, other than some phase differences, if the seismic source had been a short duration explosive such as dynamite.

Crosscorrelation is not the only method by which a known or unknown long time-duration signal can be extracted from a second digital time series, it is used here as an example. An alternative method of extracting similar signals from among multiple data sources is Eigenvector analysis or principle components analysis. Such methods are represented herein by the crosscorrelation method but will be understood by practitioners versed in geophysical methods that any method of similar signal extraction and quantification are applicable in application of this invention. Eigenstructure decomposition or semblance methods are applicable for signal analysis methods for embodiments.

Figure 2:
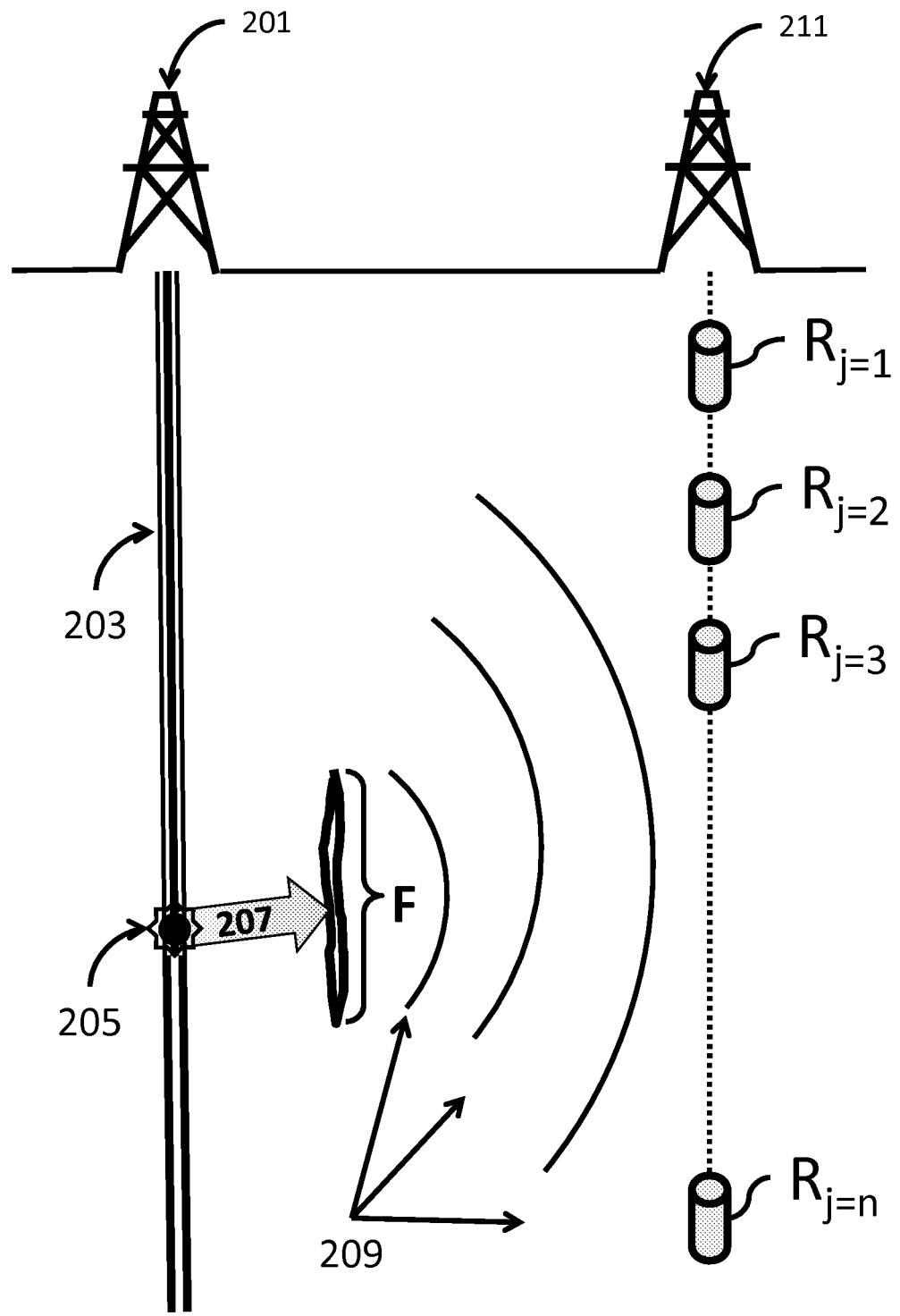
FIG. 2 illustrates schematically a model for fluids flowing through a fracture. Fractures may be naturally occurring or created by fracture stimulation. Fluids flowing through fractures generate seismic wave fields that propagate through the surrounding rock mass and are recorded by seismic sensors. The seismic waves will be generated for the time during which fluids flow through the fracture. Fracture simulation treatments often last for several hours and fluids can flow through a reservoir for decades.

Fluids flowing through confined fractures resonate, vibrate, and otherwise generate seismic signals for the time duration in which fluids are flowing and interacting with the formation. FIG. 2 shows a 2-dimensional cross sectional view of the earth's otherwise 3-dimensional subsurface. The derrick symbol 201 represents any surface facilities associated with a well operation, including but not limited to drilling, completing, producing, hydrofracturing, logging or installing monitoring sensors. The well bore 203 in this example is used to pump fluids that are injected into the subsurface at port 205 that are illustrated schematically to flow 207 through arbitrary fracture F.

A point or opening "F" in FIG. 2 represents a location at which fluid flow 207 enters a fracture or confined space and is a location from which a seismic signal radiates, thereby emitting seismic wave fronts 209, over a relatively long time period while fluid is moving through the fracture. The moving fluid will encounter many fractures, which each may emit acoustic radiation associated with the fracture position in the subsurface due to fluid movement and fracturing.

Also illustrated in FIG. 2 is a sensor array associated with a well location 211 that includes a set of downhole seismic receiver locations $R_j$ where j is the index of multiple seismic receivers at different locations shown as receiver locations j=1, 2, 3 . . . , N. In FIG. 2 the receivers are depicted geometrically as they would be in a vertical well 211 but it will be appreciated the multiple receivers may be placed in arbitrary locations in three dimensions.

Seismic receiver locations are generally assumed to be occupied by multi-component receivers with at least three mutually perpendicular sensors at each receiver location. The use of 3-component geophones or accelerometers at the receiver positions provides discriminatory power as to the actual direction from which energy arrives.

Figure 3:
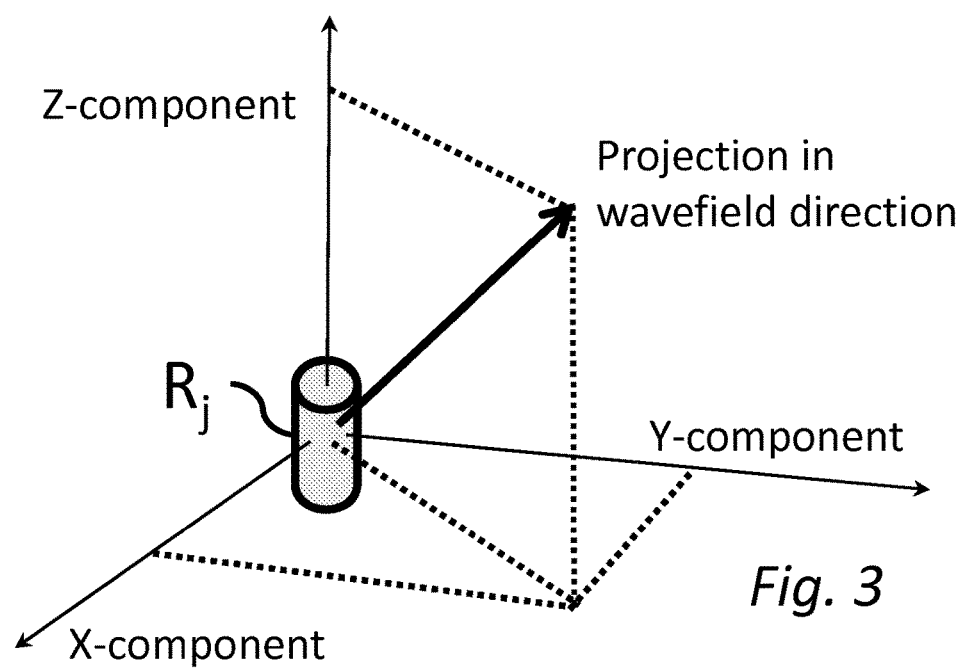
FIG. 3 illustrates a coordinate system for a 3-component geophone with orthogonal components Z, X, and Y.

FIG. 3 illustrates vectors related to an arbitrary three-component sensor $R_j$, such as a geophone or accelerometer, and shows that the projection in the wavefield direction may be determined. FIG. 3 illustrates that the direction from which compressional or shear wave acoustic energy arrives at a three-component sensor can be determined as the vector sum of simultaneously recorded seismic amplitudes. Signal processing discussed herein may take appropriate advantage of the availability of multicomponent seismic receivers, as would any prudent data processor well versed in the art of multicomponent seismic data processing, including geometric projection of data recorded on multiple receiver components onto other vector directions and separation of wave modes. The particle motion of a wave that passes by a 3-component sensor can be resolved by vector analysis of the waveforms recorded on the respective components. For example, the direction from which seismic compressional waves arrive at a geophone is the vector sum of simultaneously recorded amplitudes on the three mutually perpendicular geophone components.

Figure 4:
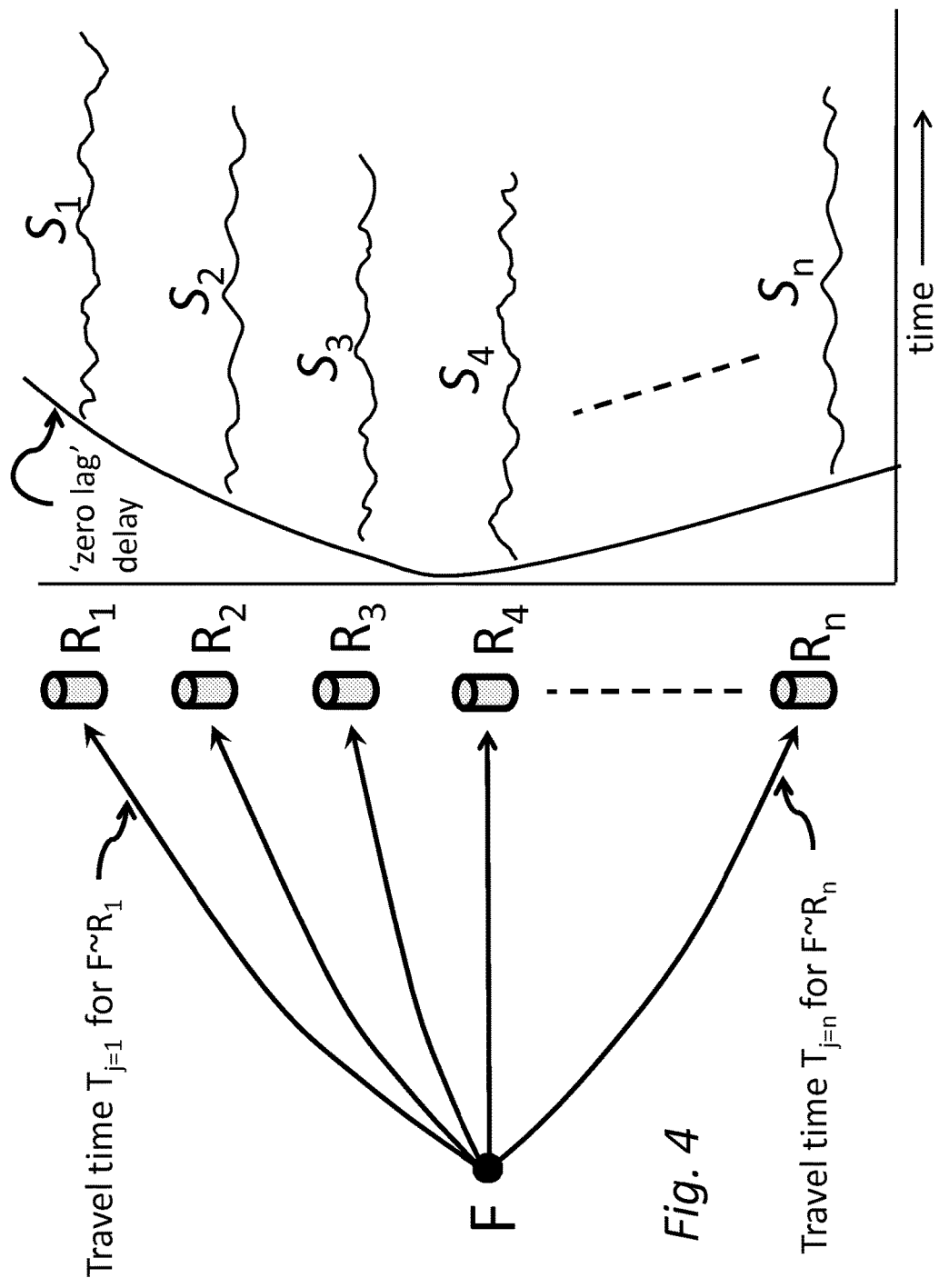
FIG. 4 illustrates schematic seismic ray paths between the point "F" and the receivers $R_i$ where the raypath is annotated $F \sim R_i$. The seismic signal originating at fracture or fluid flow acoustic energy source F will be recorded at each of the seismic receiver locations $R_1$ to $R_n$. The associated seismic ray path travel time from the point F to a receiver at $R_n$ is annotated as $T_n$.

The seismic wavefield produced at a point F, which represents the position of the source of an acoustic wave emission, will travel to each of the seismic receivers $R_j$ in a time represented here as $T_j$ (FIG. 4). The seismic signal originating at point F is recorded at receiver sondes $R_1$ through $R_N$ as time series $S_1$ through $S_N$, respectively. The seismic travel raypath from a point F to a point $R_j$ is annotated in FIG. 4 as F~$R_j$. The travel time from F to each receiver can be estimated via travel time computations that use any known velocity information derived from any a priori or contemporaneously acquired information including perforation shots, string shots, and geologic structure. In FIG. 4 the seismic signal from F arrives at each sensor at various but predictable times. In all real cases the seismic signal arriving from F will be contemporaneous over time with other signals and noise from other sources. The seismic travel time difference between the common signal arriving at receivers $R_i$ and $R_k$ from the point F is expressed as $T_i-T_k=Z_{ik}$. Said another way, the value of $Z_{ik}$ is the travel time difference between the seismic raypaths F~$R_i$ and F~$R_k$. The notation $S_i$ indicates the seismic data time series recorded at receiver index "i".

Suppose now that the seismic signal generated at F is recorded at two separate receivers, arbitrarily designated $R_i$ and $R_k$, generating the seismic data time series $S_i$ and $S_k$ respectively over a time period P. Crosscorrelation of the seismic records $S_i$ and $S_k$ over the time period P results in a time series, $C_{ik}$. Provided that other seismic signals are nullified or largely suppressed by the crosscorrelation process, the value of $C_{ik}$ at the crosscorrelation lag time $Z_{ik}$ is proportional to the total energy recorded at the receivers $R_i$ and $R_k$ that was transmitted from the fracture or fluid flow seismic signal location, F. Said another way, the crosscorrelation process will have extracted a representation of the signal energy from F that reached the two receivers $R_i$ and $R_k$ with a time delay of $Z_{ik}=T_i-T_k$ over the time period P.

Seismic record $S_i$ is crosscorrelated with seismic record $S_k$ over time period P, wherein the time lag between $S_i$ and $S_k$ is $Z_{ik}$. The time lag $Z_{ik}$ is determined by the time difference of the raypath from the sensor recording $S_i$ and the raypath from the sensor recording $S_k$. The relative time lags between all records $S_{j=1\ to\ n}$ form a time surface ('zero lag' delay) that is a function of the position of F, the position of the sensors and the velocity field.

Further discriminatory power of the signal received from the point F can be achieved by forming the sum $$f(F)=\Sigma C_{ij}(Z_{ij}) \quad \text{Equation 2}$$

in which ij represents all possible pairs of receiver locations and $Z_{ij}$ is the appropriate time delay determined from the zero lag of the crosscorrelation (or similar signal extraction or quantification method). For example, other signal extraction or quantification methods include eigenstructure decomposition algorithms that use a plurality of receivers will also give results that may be more sensitive to waveforms compared to crosscorrelation or multichannel semblance algorithms, which may also be used.

Figure 5:
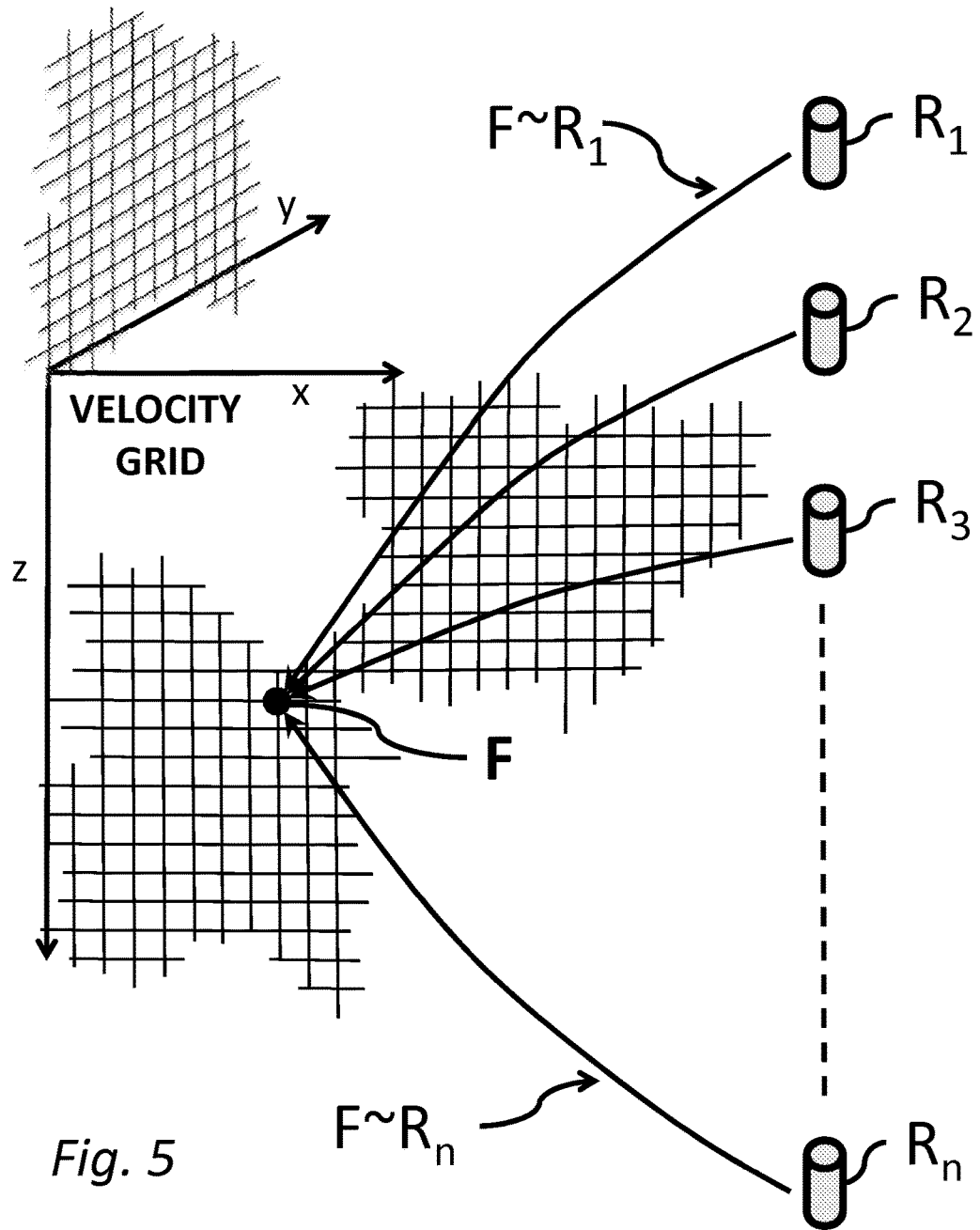
FIG. 5 illustrates the inverse seismic wave paths from sensors to potential fracture position F with a velocity model or grid (schematically represented by a partial mesh) for travel paths from sensors $R_1$ to $R_n$ using one or more embodiments of the methods disclosed herein. Seismic ray path times $T_1$ to $T_n$ may be used to determine potential 'zero-lag' values for crosscorrelation or initial times for determining data sequences for input to algorithms for determining node coefficient values, such as signal subspace methods.

The process described relative to FIG. 4 is further shown in FIG. 5 using a velocity grid for determining travel times between receivers and subsurface positions and the time delay between receivers $R_1$ to $R_n$ and a position in the grid, for example an arbitrary subsurface position F in x, y and z space. While grid positions are schematically illustrated for the Velocity Grid (which while partially illustrated impliedly covers the entire raypath space), all positions are used for a 3-D velocity model. As is well known to practitioners of the geophysical imaging arts, other coordinate systems and geometries may be advantageously used depending on the configurations of the sensors and subsurface structure and properties.

Figure 6:
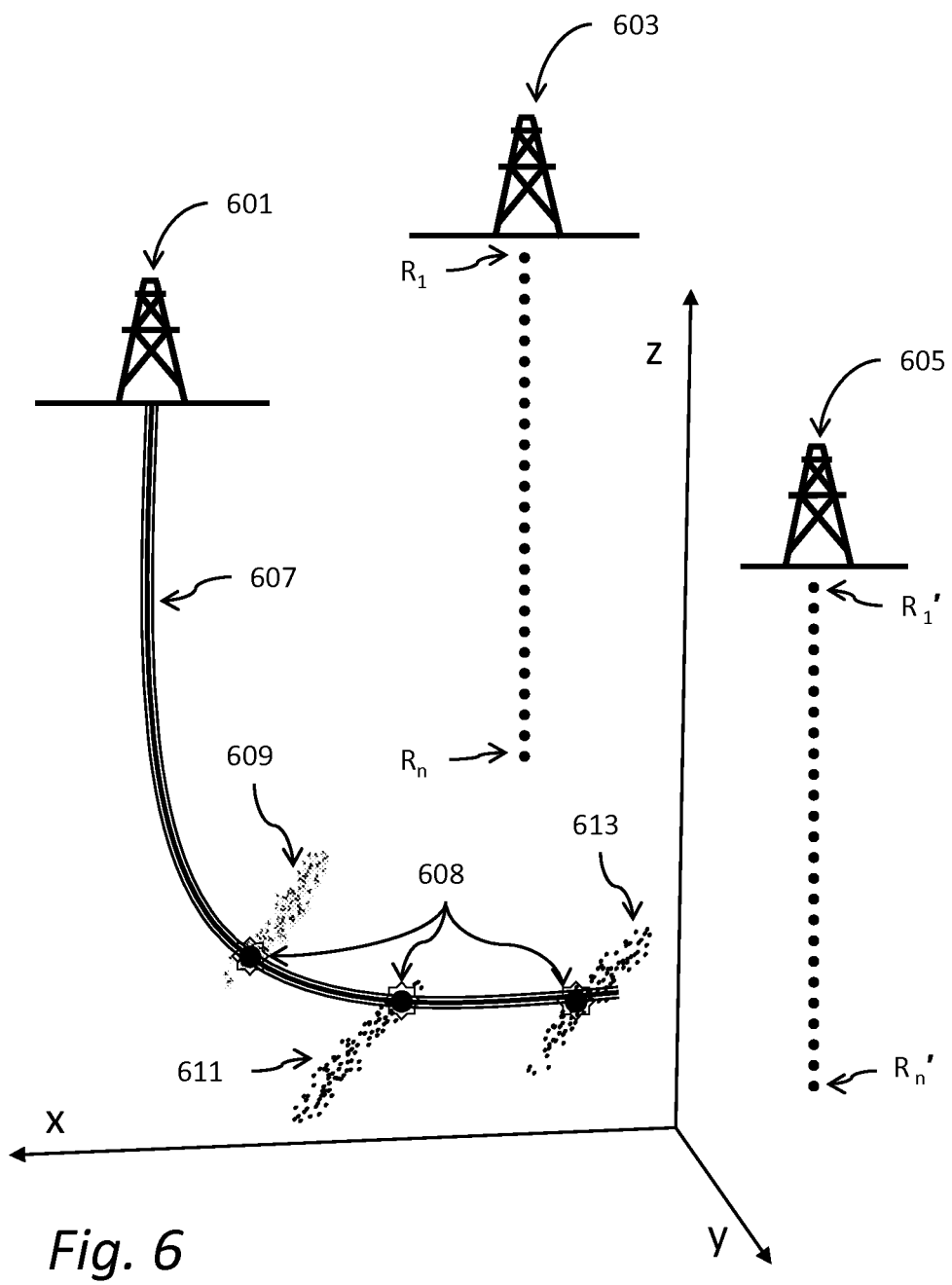
FIG. 6 illustrates acoustic source points representing the highest amplitudes found in the grid space as determined from fluid flow determination using one or more embodiments of the methods disclosed herein.

FIG. 6 illustrates an example arrangement for detecting and locating fluid flow. The fluid flow location process described using Equation 2 with a subsurface model or grid can be applied to focus multiple seismic receivers toward any and all points in a volume to determine an acoustic energy representation value f(F) or "f" for points of interest in the volume. Well location 601 represents a fracture-treatment well that includes well bore 607 with ports 608 for injecting fluids into the earth at various locations along the well bore. Well location 603 represents a bore hole with monitoring sensors $R_1$ to $R_n$ that record seismic data $S_1$ to $S_n$. Optionally more monitoring arrays may be used as well, for example well location 605 including sensors $R_1'$ to $R_n'$ that record seismic data $S_1'$ to $S_n'$. Relative time lags $Z_{ik}$ are computed for sensor pairs for various time periods P. Sensor recordings $S_1$ to $S_n$ are crosscorrelated using $Z_{ik}$ to determine coefficients $C_{ij}$ related to the subsurface positions.

The acoustic energy representation value of f(F) in Equation 2 is computed for grid locations in the vicinity of the well bore 607 around ports 608. The areas 609, 611 and 613 depicted as clouds of dots are clusters of values above a threshold value. These areas represent fluid flow locations and may be displayed so that the inherent dynamic fluid flow information within the data is depicted relative to time. For example the values at each position may be displayed and/or displayed relative to time or time-relative coloring or value-relative coloring may be associated with the fluid flow locations and associated values.

The volume areas 609, 611 and 613 are depicted for simplicity of this illustration as discrete static positions in FIG. 6 which are above a threshold value of f. The dynamic variability in the values of f at a subsurface position in the vicinity of well bore 607 may also be represented as relative values. Values or points as shown in FIG. 6 can be generated for various or progressive time periods, P, thus displays of how fluid flows through a rock volume over time can be created. Petroleum engineers can use this information to optimize well completion operations and maximize efficiency of reservoir drainage.

Figure 7:
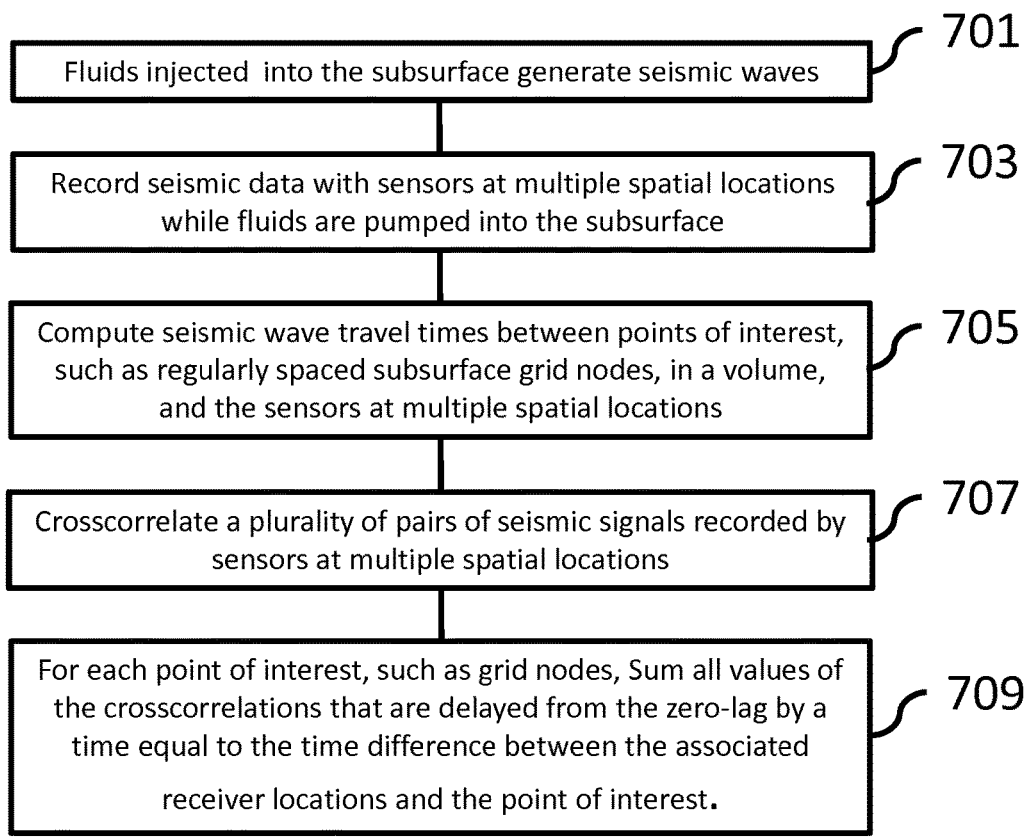
FIG. 7 is a flow chart illustrating a non-limiting embodiment of methods disclosed in the present disclosure.

FIG. 7 illustrates a flowchart of a nonlimiting embodiment wherein fluids are injected into the subsurface in proximity to a reservoir or potential reservoir, the fluid injection generating seismic waves 701. Seismic data are recorded with sensors at multiple spatial locations before, during and after fluids are pumped into the subsurface 703. Traveltime for seismic waves are computed between grid nodes representing subsurface positions and seismic sensors 705. Pluralities of pairs of seismic signals are crosscorrelated 707. For subsurface positions of interest (represented by grid nodes) the values derived from the crosscorrelations that are delayed from a zero lag by a time equal to the time difference between the associated receiver locations and the subsurface position 709 (or point of interest).

Figure 8:
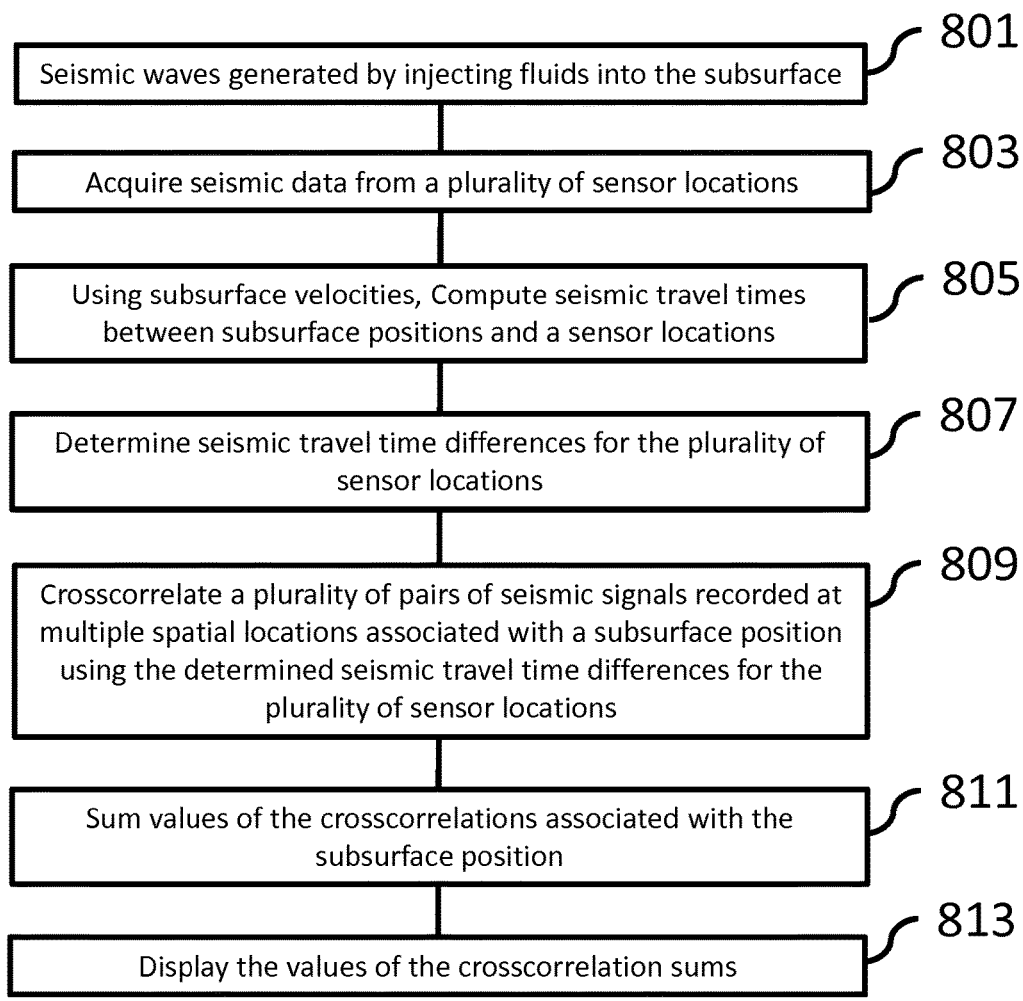
FIG. 8 is a flow chart illustrating a non-limiting embodiment of methods disclosed in the present disclosure.

FIG. 8 illustrates a flowchart of a nonlimiting embodiment wherein seismic waves are generated in the subsurface during fluid injection 801. Seismic data are acquired from a plurality of sensor locations 803. Seismic wave travel times are computed using subsurface velocities between subsurface positions and the plurality of sensor locations 805. Seismic travel time differences are determined for the plurality of sensor locations 807. A plurality of pairs of seismic signals is crosscorrelated from multiple sensor locations for a subsurface position 809. The values of the crosscorrelations are summed 811. The summed values of the crosscorrelations may be displayed 813. The summed values, a representation of the energy emanating from a subsurface location, may be displayed by position or by position relative to time.

Figure 9:
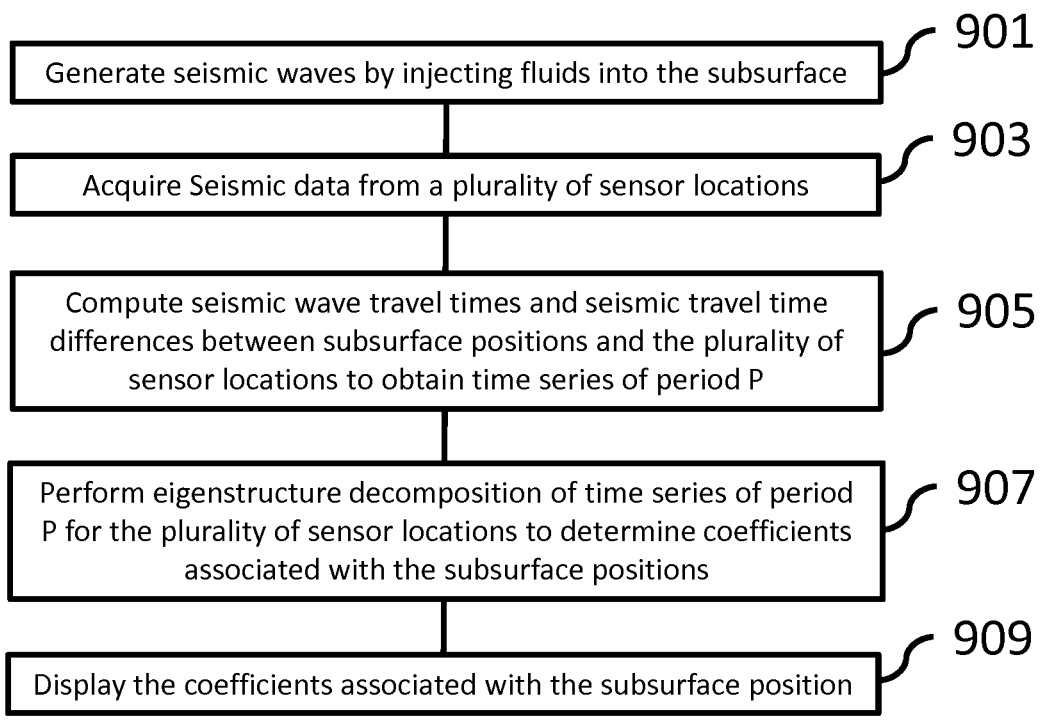
FIG. 9 is a flow chart illustrating a non-limiting embodiment of methods disclosed in the present disclosure.

FIG. 9 illustrates a flowchart of a nonlimiting embodiment wherein seismic waves are recorded that are generated during operations injecting fluids into the subsurface 901. Seismic data are acquired from a plurality of sensor locations 903. Using subsurface velocities, compute seismic wave travel times and relative seismic travel time differences between subsurface positions and the plurality of sensor locations to obtain associated time series of period P, 905. Perform eigenstructure decomposition of associated time series of period P for the plurality of sensor locations to determine coefficients associated with the subsurface positions 907. Display the coefficients associated with the subsurface position 909.

In one nonlimiting embodiment a method for a method for determining a fluid flow seismic signal position in the subsurface comprises acquiring seismic data from a plurality of sensors, computing travel times between a subsurface position and the plurality of sensors computing travel time differences for the seismic data between the plurality of sensor locations and the subsurface position, obtaining seismic data similarity coefficients associated with the subsurface position using the computed seismic travel time differences and summing the obtained similarity coefficients to obtain a fluid flow seismic signal value associated with the subsurface position.

In other aspects a method for determining fluid flow further comprises obtaining seismic data similarity coefficients using cross correlation of a plurality of pairs of seismic signals. Other aspect include obtaining seismic data similarity coefficients using eigenstructure decomposition or determining the coefficients using semblance calculations. Computing travel times further comprises using velocities derived from at least one selected from the group consisting of i) a perforation shot, ii) a string shot, iii) surface seismic data, iv) a check shot and v) VSP data. The data for determining fluid flow may comprise data acquired while fluids are injected into subsurface formations through a port in a well bore. The sensors may be three-component sensors. The obtained coefficients associated with subsurface locations may be stored on electronic media in a form for display.

In another nonlimiting embodiment an information handling system for determining fluid flow seismic signal positions in the subsurface is associated with acquired seismic data and comprises a processor configured for computing travel time differences between a subsurface position and a plurality of sensors used in acquiring the seismic data, a computer readable medium for storing travel time differences for the seismic data between the plurality of sensor locations and the subsurface position, processing obtained seismic data similarity coefficients associated with the subsurface position using the computed seismic travel time differences and summing the obtained similarity coefficients to obtain a fluid flow seismic signal value associated with the subsurface position.

In still another aspect the processor is configured to obtain seismic data similarity coefficients associated with the subsurface position using the computed seismic travel time differences. The information handling system further comprises a display device for displaying the seismic data similarity coefficients. Similarity coefficients may be determined using cross correlation of a plurality of pairs of seismic signals, eigenstructure decomposition or semblance calculations. A graphical display coupled to the processor and configured to present a view of the summed seismic data similarity coefficients is another aspect.

In still another embodiment a set of application program interfaces is embodied on a computer readable medium for execution on a processor in conjunction with an application program for processing synchronized seismic data array measurements to determine subsurface fluid movement by locating a fluid flow seismic signal position comprising a first interface that receives synchronized seismic data array measurements, a second interface for computing travel times between a subsurface position and the plurality of sensors; a third interface for computing travel time differences for the seismic data between the plurality of sensor locations and the subsurface position, a fourth interface for cross correlating seismic data using the computed seismic travel time differences from the plurality of sensors to obtain coefficients associated with the subsurface position and summing the obtained coefficients from the plurality of sensors to obtain a fluid flow seismic signal value associated with the subsurface position.

In another aspect the set of application interface programs further comprises a cross correlation interface that receives instruction data for applying a cross correlation of a plurality of pairs of seismic signals to the synchronized array measurements. Another aspect comprises an eigenstructure decomposition interface that receives instruction data for applying an eigenstructure decomposition interface to the synchronized array measurements. Still another aspect comprises a semblance analysis interface that receives instruction data for applying semblance analysis to the synchronized array measurements. Yet another aspect comprises using velocities derived from a perforation shot, a string shot, surface seismic data, a check shot or VSP data. In still another aspect the set of application interface programs comprises an interface for processing data acquired while fluids are injected into a subsurface formation through a port in a well bore. In another aspect the set of application interface programs may comprise an interface for processing data acquired while fluids are injected into a subsurface formation through a port in a well bore. Yet another aspect includes an application interface comprising for storing the obtained coefficients associated with subsurface locations in a form for display.

In another embodiment a method of determining fluid flow seismic signal positions in the subsurface comprises acquiring seismic data from a plurality of sensors, computing travel times between a plurality of subsurface positions and the plurality of sensors, computing travel time differences for the seismic data between the plurality of sensor locations to the plurality of subsurface positions, determining seismic data coefficients for the seismic data between the plurality of sensor locations to the plurality of subsurface positions using eigenvalue decomposition to obtain a fluid flow seismic signal value associated with each of the plurality of the subsurface positions.

In another aspect the method of determining fluid flow includes computing travel times further comprising using velocities derived from a perforation shot, a string shot, surface seismic data, a check shot or VSP data. In another aspect the method comprises acquiring the seismic data while fluids are injected into subsurface formations through a port in a well bore. In another aspect the sensors are three-component sensors. The obtained coefficients associated with subsurface locations may be stored in a form for display.

In still another embodiment a method of determining subsurface fluid movement by locating a fluid flow seismic signal position comprises acquiring seismic data from a plurality of sensors, computing travel times between a subsurface position and the plurality of sensors, computing travel time differences for the seismic data between the plurality of sensor locations and the subsurface position, cross correlate seismic data using the computed seismic travel time differences from the plurality of sensors to obtain coefficients associated with the subsurface position and summing the obtained coefficients from the plurality of sensors to obtain a fluid flow seismic signal value associated with the subsurface position.

In another aspect the method includes computing travel times comprising using velocities derived from a perforation shot, a string shot, surface seismic data, a check shot or VSP data. In yet another aspect the seismic data are acquired while fluids are injected into subsurface formations through a port in a well bore. In still another aspect the plurality of sensors are three-component sensors. And in another aspect the obtained coefficients associated with subsurface locations are stored in a form for display.

Figure 10:
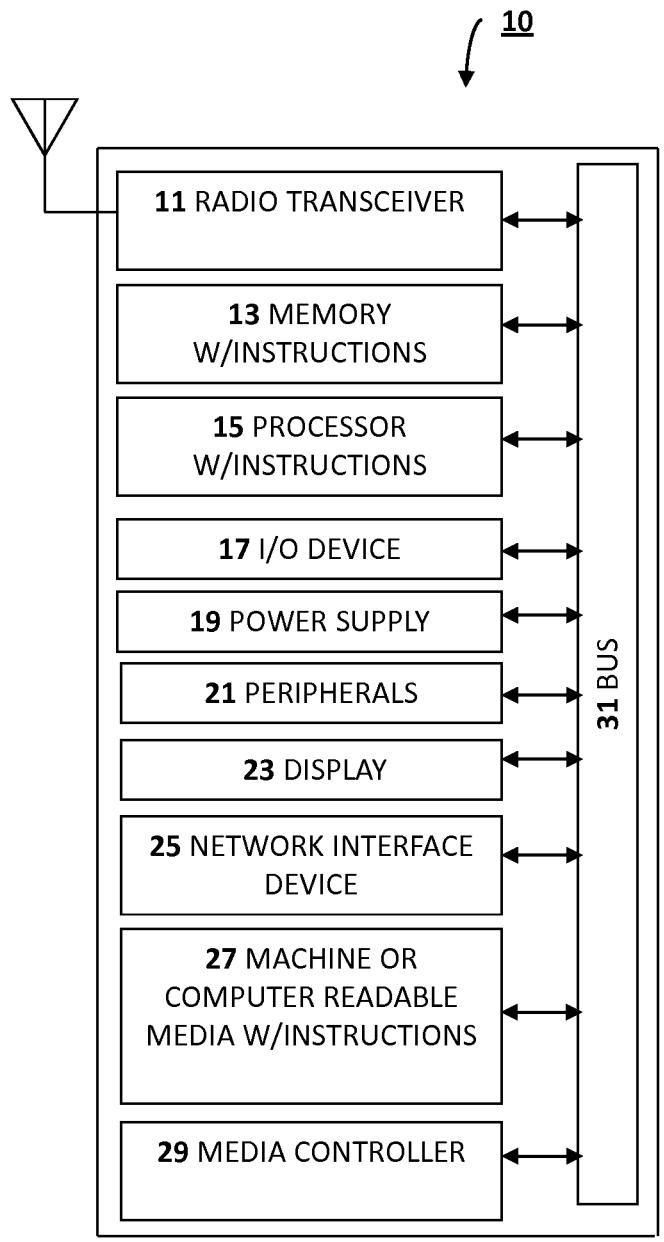
FIG. 10 illustrates an embodiment of a seismic data processing system within which a set of instructions may enable the system to perform any of the nonlimiting embodiments or their equivalents disclosed herein, including sets of application program interfaces.

An example of a seismic data processing system is illustrated with FIG. 10, an embodiment of a seismic data processing system within which a set of instructions may enable the system to perform any of the nonlimiting embodiments or their equivalents disclosed herein for determining the location of fluids flowing in the earth. A seismic data processing system may be a standalone system, computer, host computer, server or blade, or may be connected to other systems within a network. Seismic data processing system 10 may include a radio transceiver 11 connected to an antenna for providing wireless access to systems, networks and devices. In a networked deployment, the seismic data processing system may operate as a server or a client in server-client networked environment or as a member of a distributed network environment. Memory 13 may be volatile or non-volatile memory with instructions, programs and data. One or more central processing units (CPU) 15 or other processors including parallel processors may be included with instructions. The instructions may at least partially reside within the memory 13 and/or within the processor 15 during execution. Memory 13 and processor 15 may include machine-readable media.

Machine-readable media includes solid-state memory such as cards or other non-volatile memories, random access memories or other volatile memories, magneto-optical or optical media (e.g., disk or tape), or signals embodying computer instructions in a transmission medium. A machine-readable medium for the embodiments disclosed herein includes equivalents and successor media.

An input/output device 17 is provided to send data to, or receives data from, other system components or devices. At least one seismic data processing system bus 31 provides communication between and among components.

Additionally, seismic data processing system 10 may include peripherals 21 (keyboards, GPS receivers, USB adapter, headphones, microphone, wireless audio transmitter, print adapter, mouse, serial adapter, etc). Various types of display device 23 may be attached or linked with seismic data processing system 10. Network interface equipment such as Network Interface Controller 25 (NIC) may provide hardwired access to infrastructure. Other interfaces may include a PCI bus, and USB ports, etc. A machine readable medium with instructions 27 may be on a disk drive device and provide additional software and data storage capability to seismic data processing system 10.

For example, computer readable medium 27 and memory 13 may include programs to process seismic data, which may be stored as program data and seismic data, according to the methods disclosed herein. The application program associated with the computer readable medium 27 may include at least one application program interface for receiving and/or processing seismic data. The program data may include seismic data acquired for processing according to embodiments disclosed herein. A set of application program interfaces residing on computer readable medium 27 or memory 13 may include at least one application interface associated with calculating fluids flowing in subsurface reservoirs or processing data to locate associated temporal changes in subsurface reservoirs, or for determining other subsurface hydrocarbon reservoir parameters.

Processor 15 may carry out graphics/memory controller hub functions and enable input/output (I/O) functions for I/O device 17 and associated peripherals 21. Peripherals 21 such as a mouse, keyboard, and tablet are also coupled to other components at the option of the user. The seismic data processing system bus 31 may connect to I/O devices 17. Non-limiting examples of a seismic data processing system bus may include a Peripheral Component Interconnect (PCI) bus, PCI Express bus, SATA bus or other bus is coupled to enable seismic data processing system bus 31 to be connected to other devices which provide seismic data processing system 10 with additional functionality. A universal serial bus (USB) or other I/O bus may be coupled to seismic data processing system bus 31 to facilitate the connection of peripheral devices 21 to seismic data processing system 10. System basic input-output system (BIOS) may be coupled to processor 15. BIOS software is stored in nonvolatile memory 13 such as CMOS or FLASH memory. A network interface controller (NIC) 25 is coupled to processor 15 to facilitate connection of system 10 to other data, information or seismic data processing systems. A media drive controller 29 is coupled to processor 15 through bus 31. An example of a media drive controller may include a baseboard management controller (BMC). Devices that can be coupled to media drive controller 29 include CD-ROM drives, DVD drives, hard disk drives and other fixed or removable media drives. It should be understood that the technology disclosed herein is not only applicable to the embodiment of FIG. 10 but is also applicable to the other types of seismic data processing systems.

While various embodiments have been shown and described, various modifications and substitutions may be made thereto without departing from the spirit and scope of embodiments illustrated in this disclosure. Accordingly, it is to be understood that various embodiments of the present invention have been described by way of illustrations and not limitation.

What is claimed is:

1. A method, comprising: placing a plurality of sensors into a subsurface underneath of at least one surface facility at a respective plurality of subsurface positions in the subsurface; performing, by the at least one surface facility, an initial fracture stimulation treatment, comprising: i) injecting, by the at least one surface facility, at least one fluid, through one or more wellbores, at one or more subsurface positions associated with a reservoir of hydrocarbons; ii) acquiring, by a processor, for a duration of at least 10 minutes, a plurality of seismic traces from the plurality of sensors located in the subsurface to form seismic data; wherein the plurality of seismic traces has respective amplitudes that are lower than amplitudes of seismic waves caused by a microseismic event; iii) computing, by the processor, from the seismic data, seismic wave travel times between the one or more subsurface positions within the subsurface and a subset of the plurality of sensors located at a respective plurality of sensor subsurface positions in the subsurface; iv) computing, by the processor, from the computed seismic wave travel times, seismic wave travel time differences between the subset of the plurality of sensors located at the respective plurality of sensor subsurface positions in the subsurface and the one or more subsurface positions; v) determining, by the processor, seismic data similarity coefficients associated with the one or more subsurface positions based at least in part on the computed seismic wave travel time differences; vi) determining, by the processor, based at least in part on the determined seismic data similarity coefficients, a fluid flow seismic signal value associated with the one or more subsurface positions; wherein the fluid flow seismic signal value is distinct from seismic event data resulting from a tensile failure; vii) determining, by the processor, at least one position of a fluid front of the at least one fluid moving through the subsurface based at least in part on the fluid flow seismic signal value associated with the one or more subsurface positions; and performing, by the at least one surface facility, based at least in part on the at least one position of the fluid front of the at least one fluid moving through the subsurface, one or more remedial activities to drain one or more parts of the reservoir of hydrocarbons that are not fractured by the initial fracture stimulation treatment, wherein the one or more remedial activities comprise i) drilling one or more additional wellbores at one or more additional subsurface positions associated with the one or more parts of the reservoir of hydrocarbons and ii) performing one or more subsequent fracture stimulation treatments, wherein the at least one or more remedial activities further comprise: i) adjusting a fluid saturation of the at least one fluid, and ii) adjusting a pressure under which the at least one fluid is injected.

2. The method of claim 1, wherein the determining seismic data similarity coefficients further comprises:
    determining the seismic data similarity coefficients using a cross correlation of a plurality of pairs of seismic signals.

3. The method of claim 1, wherein the determining seismic data similarity coefficients further comprises:
    determining the seismic data similarity coefficients using an eigenstructure decomposition.

4. The method of claim 1, wherein the determining seismic data similarity coefficients further comprises:
    determining the seismic data similarity coefficients using at least one semblance calculation.

5. The method of claim 1, wherein the computing seismic wave travel times further comprises:
    using velocities derived from at least one selected from the group consisting of: i) a perforation shot, ii) a string shot, iii) surface seismic data, iv) a check shot, and v) VSP data.

6. The method of claim 1, wherein at least one sensor of the plurality of sensors is a three-component sensor.

7. The method of claim 1, further comprising:
    generating, by the processor, based at least in part on the fluid flow seismic signal value associated with the one or more subsurface positions, at least one visual representation that is distinct from the seismic event data resulting from the tensile failure.

8. A system, comprising: at least one surface facility; wherein the at least one surface facility is configured to: 1) perform an initial fracture stimulation treatment, comprising: injecting at least one fluid, through one or more wellbores, at one or more subsurface positions associated with a reservoir of hydrocarbons, and 2) perform, based at least in part on at least one position of a fluid front of the at least one fluid moving through a subsurface: one or more remedial activities to drain one or more parts of the reservoir of hydrocarbons that are not fractured by the initial fracture stimulation treatment, wherein the one or more remedial activities comprise: i) drilling one or more additional wellbores at one or more additional subsurface positions associated with the one or more parts of the reservoir of hydrocarbons and ii) performing one or more subsequent fracture stimulation treatments; a plurality of sensors placed into a subsurface underneath of the at least one surface facility at a respective plurality of subsurface positions in the subsurface; and a seismic data processing unit, comprising: a non-transient computer memory, electronically storing computer executable program code; and a processor that, when executing the particular program code, is configured to: i) acquire, for a duration of at least 10 minutes, a plurality of seismic traces from the plurality of sensors located in the subsurface to form seismic data; ii) compute, from the seismic data, seismic wave travel time differences between the one or more subsurface positions within the subsurface and a subset of the plurality of sensors located at a respective plurality of sensor subsurface positions in the subsurface; iii) compute, from the computed seismic wave travel times, seismic wave travel time differences between the subset of the plurality of sensors located at the respective plurality of sensor subsurface positions in the subsurface and the least one or more subsurface positions; iv) determine seismic data similarity coefficients associated with the one or more subsurface positions based in part on the computed seismic wave travel time differences; v) determine, based at least in part on the determined seismic data similarity coefficients to obtain, a fluid flow seismic signal value associated with the one or more subsurface positions, wherein the fluid flow seismic signal value is distinct from seismic event data resulting from a tensile failure; and vi) determine the at least one position of the fluid front of the at least one fluid moving through the subsurface based at least in part on the fluid flow seismic signal value associated with the least one or more subsurface positions, wherein one or more remedial activities further comprise: i) adjusting a fluid saturation of the at least one fluid, and ii) adjusting a pressure under which the at least one fluid is injected.

9. The system of claim 8, wherein the processor is further configured to determine the seismic data similarity coefficients by using a cross correlation of a plurality of pairs of seismic signals.

10. The system of claim 8, wherein the processor is further configured to determine the seismic data similarity coefficients by using an eigenstructure decomposition.

11. The system of claim 8, wherein the processor is further configured to determine the seismic data similarity coefficients by using at least one semblance calculation.

12. The system of claim 8, the processor is further configured to compute the seismic wave travel times by using velocities derived from at least one selected from the group consisting of: i) a perforation shot, ii) a string shot, iii) surface seismic data, iv) a check shot, and v) VSP data.

13. The system of claim 8, wherein at least one sensor of the plurality of sensors is a three-component sensor.

14. The system of claim 8, wherein the processor is further configured to generate, based at least in part on the fluid flow seismic signal value associated with the one or more subsurface positions, at least one visual representation that is distinct from the seismic event data resulting from the tensile failure.

\* \* \* \* \*